United States Patent [19] [11] 4,159,994
Seto et al. [45] Jul. 3, 1979

[54] KAOLIN INTERCALATION COMPLEXES AND PROCESSES FOR FORMING THE SAME

[75] Inventors: Herbert Seto, Orleans; Maria I. Cruz, Marcilly en Villette; Jose J. Fripiat, Orleans, all of France

[73] Assignee: Unibra Societe Anonyme, Brussels, Belgium

[21] Appl. No.: 874,603

[22] Filed: Feb. 2, 1978

[30] Foreign Application Priority Data
Feb. 4, 1977 [GB] United Kingdom ............... 04642/77
Nov. 1, 1977 [GB] United Kingdom ............... 45392/77

[51] Int. Cl.$^2$ ............................................... C07F 5/06
[52] U.S. Cl. .............................. 260/448 C; 252/49.7; 252/351; 252/455 R
[58] Field of Search ..................... 260/448 C

[56] References Cited
U.S. PATENT DOCUMENTS

| | | | |
|---|---|---|---|
| 2,531,427 | 11/1950 | Hauser | 260/448 C |
| 2,767,177 | 10/1956 | Erickson | 260/448 C |
| 2,859,234 | 11/1958 | Clem | 260/448 C |
| 2,951,087 | 8/1960 | Hauser | 260/448 C |
| 3,014,871 | 12/1961 | Fulton et al. | 260/448 C |
| 3,228,969 | 1/1966 | Kerr | 260/448 C |
| 3,306,922 | 2/1967 | Barrer et al. | 260/448 C |
| 3,350,429 | 10/1967 | Hasegawa et al. | 260/448 C |
| 3,699,139 | 10/1972 | Rubin et al. | 260/448 C |
| 3,948,790 | 4/1972 | Speakman | 260/448 C |
| 4,053,493 | 10/1977 | Oswald | 260/448 C |

OTHER PUBLICATIONS

Chemical Abstracts 75 23753k (1971).
Chemical Abstracts 73 80929e (1970).
Chemical Abstracts 50 6827f (1956).
Chemical Abstracts 70 14370c (1969).
Chemical Abstracts 65 13420h (1966).
Chemical Abstracts 81 9237n (1974).
Chemical Abstracts 64 13928h (1966).
Chemical Abstracts 55 13187h (1961).
Chemical Abstracts 62 12479d (1965).
Chemical Abstracts 69 6545c (1968).
Chemical Abstracts 21 40209 (1927).

Primary Examiner—Helen M. S. Sneed
Attorney, Agent, or Firm—Sughrue, Rothwell, Mion, Zinn and Macpeak

[57] ABSTRACT

The invention concerns a new method for obtaining intercalation complexes of kaolin materials having organic compounds or radicals in their chemical structure.

The invention also concerns new intercalation complexes of kaolin materials and their use.

31 Claims, 21 Drawing Figures

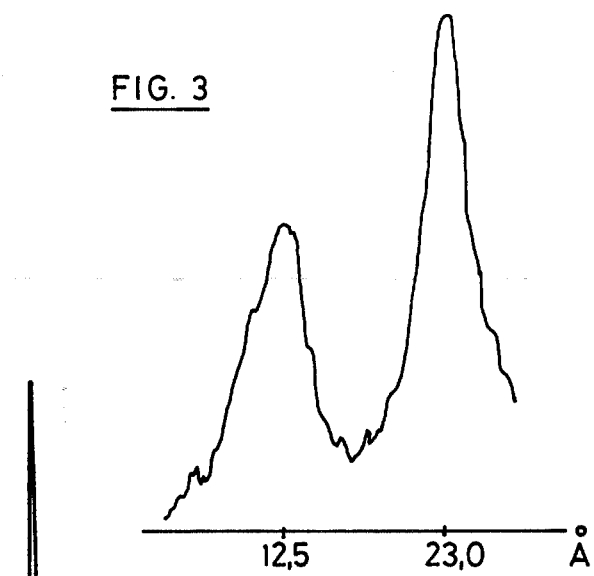
FIG. 3
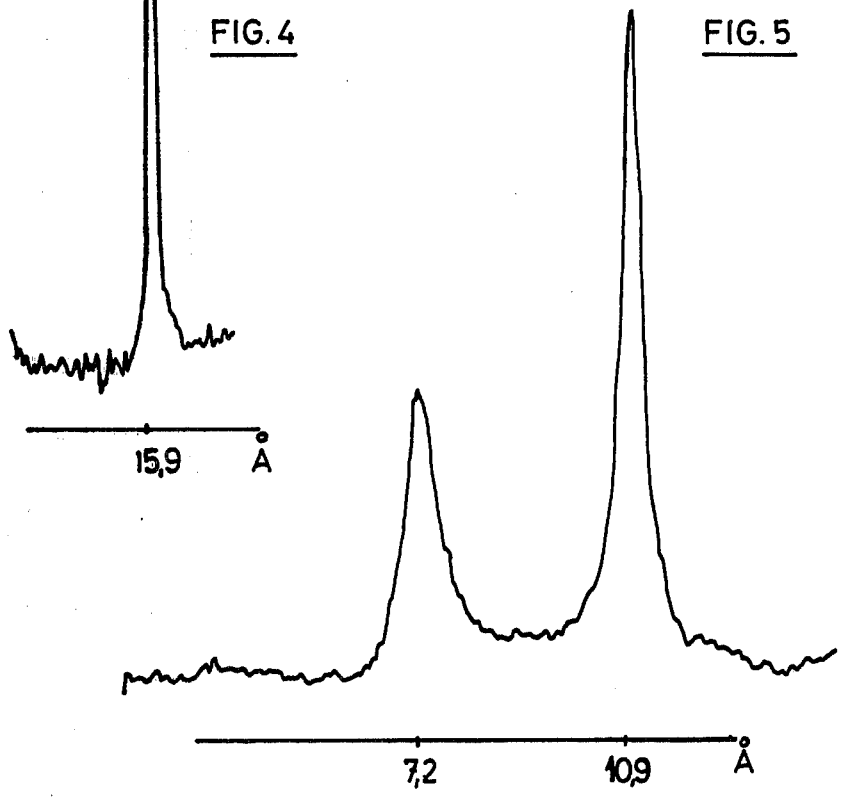
FIG. 4
FIG. 5

KAOLIN INTERCALATION COMPLEXES AND PROCESSES FOR FORMING THE SAME

BRIEF DESCRIPTION OF THE INVENTION

The present invention relates to a process for preparing intercalation complexes of kaolin materials having organic compounds or radicals in their chemical structure, said compounds or radicals being selected from
the ammonium salts of carboxylic acids having more than two carbon atoms,
the alkali metal salts of carboxylic acids having more than two carbon atoms,
the lower alkylene glycols of formula

$$HO-CH_2-(CH_2)_n-CH_2-OH \qquad (II)$$

in which n=0 to 4,
and the quaternary ammonium radicals of formula

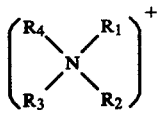

$$\begin{pmatrix} R_4 & & R_1 \\ & N & \\ R_3 & & R_2 \end{pmatrix}^+ \qquad (I),$$

in which $R_1$, $R_2$, $R_3$ and $R_4$ each represent a group selected from the aliphatic and aromatic hydrocarbon radicals, as well as stabilized derivatives of said intercalation complexes.

This invention further relates to new intercalation complexes of kaolin materials which comprise in their chemical structure a compound or radical selected from the ammonium salts of carboxylic acids having more than two carbon atoms, the lower alkylene glycols of formula II,
the quaternary ammonium radicals of formula I, in which $R_1$, $R_2$, $R_3$ and $R_4$ have the meanings given hereabove, and to a new type or form of the intercalation complexes of kaolin materials which comprise in their chemical structure an alkali metal salt of a carboxylic acid having more than two carbon atoms.

The invention further also relates to new stabilized derivatives of the new intercalation complexes of kaolin materials according to the invention.

Finally the invention also relates to the use of the intercalation complexes of kaolin materials according to the invention, and their stabilized derivatives according to the invention, more specifically to the use of said complexes and said stabilized derivatives thereof as absorbing agents, as organic dispersing agents, as coating agents and/or as lubricating agents, and as intermediates for other reactions.

BACKGROUND OF THE INVENTION

The expansion of kaolin materials leads to an increase of the division stage of the clay, not by a grinding process but by a process of de-lamellation. The initial microcrystal consisting of parallel, adjacent two dimensional layers having the general composition $Al_2O_3$—$2SiO_2$—$2H_2O$ is transformed into a microcrystal which has approximately the same composition and morphology, but between the layers of which certain molecules have been introduced.

In this manner, the accessible surface area increases from about 20 to about 800 m2/g, which would correspond for spherical particles to decrease their cross section by a factor of 40 (for instance by grinding).

Intercalation complexes of montmorillonite with quaternary amines (Bentones) having specific areas of about 800 m2/g are known. These bentones are used as a loading for paintings and varnishes, as thickeners in greases, etc.

As the natural deposits of montmorillonite minerals are rather limited, and as the demand for bentones goes ever increasing, there has been considerable investigation for finding substitute products for this type of products.

The scientific literature thus discloses a kaolinite complex with potassium acetate. This kaolinite complex was prepared by grinding the clay with potassium acetate.

There is also known a hydrazine-kaolinite complex obtained by dispersing the clay in hydrazine.

There is further described an ammonium acetate complex of kaolinite which is prepared by contacting the kaolinite with a saturated ammonium acetate solution. The reaction is very sensitive to pH and temperature and is reported to be rather troublesome.

A number of specific intercalation complexes of kaolinite in the series consisting of kaolinite complexes with alkaline metal (Na, K, Rb, Cs) salts of lower aliphatic acids (acetic, propionic, butyric, isovaleric acids) have also been described. Some of these may be obtained by direct contact of the kaolinite with a saturated solution of the salt to be intercalated; others are very slow or impossible to form according to this method; another disclosed method for obtaining this specific type of intercalation complexes of kaolinite comprises using hydrazine as a "hauling agent" (German: "Schlepper") to introduce the salt into the kaolinite lattice.

DETAILED DESCRIPTION OF THE INVENTION

Figure 1A:
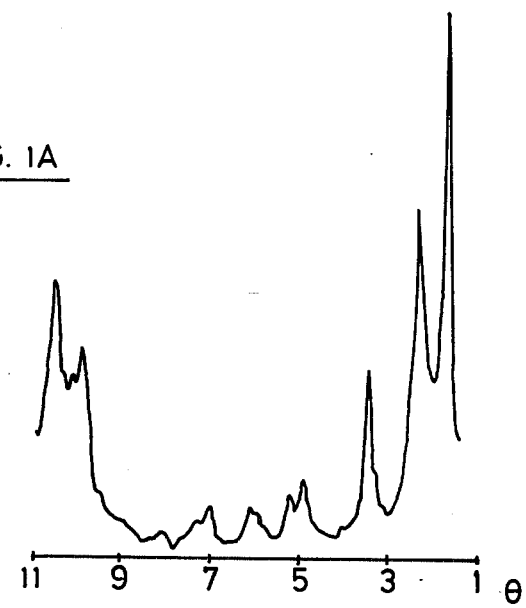

It has now been found surprisingly that it is possible to prepare intercalation complexes of kaolin materials having organic compounds or radicals in their chemical structure, said compounds or radicals being selected from the ammonium salts of carboxylic acids having more than two carbon atoms, the alkali metal salts of carboxylic acids having more than two carbon atoms,
the lower alkylene glycols of formula

$$HO-CH_2-(CH_2)_n-CH_2-OH \qquad II$$

in which n=0 to 4, and the quaternary ammonium radicals of formula

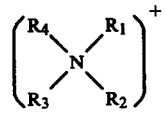

$$\begin{pmatrix} R_4 & & R_1 \\ & N & \\ R_3 & & R_2 \end{pmatrix}^+ \qquad I$$

in which $R_1$, $R_2$, $R_3$ and $R_4$ each represent a group selected from the aliphatic and aromatic hydrocarbon radicals, as well as stabilized derivatives of said intercalation complexes, by (1) reacting a kaolin-hydrazine complex either directly with a solution of an ammonium or alkali metal salt of a carboxylic acid having more than two carbon atoms, or first with an ammonium acetate solution, so as to obtain in a first reaction step a kaolin ammonium acetate complex, which is then reacted in a second reaction step with a solution of an ammonium or alkali metal salt of a carboxylic acid having more than two carbon atoms, (2) reacting possibly and further the thus obtained new complex of kaolin with an ammonium or alkali metal salt of a carboxylic acid with a lower alkylene glycol of formula II or with a quaternary ammonium salt of formula

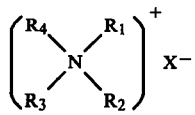

in which $R_1$, $R_2$, $R_3$ and $R_4$ have the meanings hereabove and in which X represents the anion of a mineral acid or the hydroxyl radical OH, so as to obtain a complex of kaolin having a lower alkylene glycol or a quaternary ammonium radical in its chemical structure, the obtained new intercalation complex of kaolin being possibly subjected to a flash heat treatment at a temperature of about 100° to 300° C., or to a treatment with an organic solvent, so as to obtain a stabilized derivative of said intercalation complex of kaolin.

In a first embodiment of the process according to the invention the kaolin-hydrazine complex is reacted with a saturated aqueous solution of an ammonium or alkali metal salt of a carboxylic acid having more than two carbon atoms.

According to a preferred feature of this first embodiment of the invention the kaolin-hydrazine complex is washed with one or more fractions of saturated aqueous solution of an ammonium or alkali metal salt of a carboxylic acid having more than two carbon atoms, thoroughly draining the obtained product after each operation.

Most preferably the draining operation is achieved by centrifuging the suspensions and decanting the supernatant liquid after each washing operation.

In a second embodiment of the process according to the invention the kaolin-hydrazine complex is first reacted with a saturated aqueous solution of ammonium acetate, whereafter the obtained kaolin-ammonium acetate complex is reacted with a saturated solution of an ammonium or alkali metal salt of a carboxylic acid having more than two carbon atoms.

Here also the draining operations are preferably achieved by centrifuging the suspensions and decanting the supernatant liquid after each washing operation.

Each of the above described process embodiments of the process according to the invention may be used for preparing the new organic intercalation complexes of kaolin materials with ammonium or alkali metal salts of carboxylic acids having more than two carbon atoms.

The second embodiment however may proceed more readily and allow to obtain better yields.

In still another embodiment of the process according to the invention the kaolin-hydrazine complex is first reacted with a saturated aqueous solution of an ammonium salt of a carboxylic acid having more than two carbon atoms, whereafter the obtained intercalation complex of kaolin is subjected to a flash-heat treatment at a temperature of about 100°–300° C. so as to obtain a stabilized intercallation complex of kaolin and an ammonium salt of a carboxylic acid having more than two carbon atoms.

In a further embodiment of the process according to the invention the complex of kaolin with an ammonium or alkali metal salt of a carboxylic acid having more than two carbon atoms is first reacted with an excess of a lower alkylene glycol of formula II, for at least a few minutes, preferably at room temperature, using most preferably ethylene glycol.

According to a preferred feature of this embodiment of the invention, the process step for preparing a kaolin complex of an alkylene glycol is performed by using an ammonium or potassium propionate complex of kaolin as starting material.

In particular there may be used very suitably an ammonium propionate complex of kaolinite having a (001) spacing higher than 20 Å.

In another embodiment of the process according to the invention the complex of kaolin with an ammonium or alkali metal salt of a carboxylic acid having more than two carbon atoms is first reacted with a lower alkylene glycol of formula II, whereafter the obtained intercalation complex of kaolin is subjected to a flash heat treatment at a temperature of about 100°–300° C. so as to obtain a stabilized intercalation complex of kaolin and a lower alkylene glycol.

According to preferred features of the embodiments of the invention relating to the flash-heat treatments for obtaining new stabilized complexes of kaolin with ammonium salts of carboxylic acids having more than two carbon atoms or with alkylene glycols having 2 to 6 carbon atoms, said flash heat treatments are performed at temperatures comprised between 250° and 260° C.

The operation is very suitably carried out by spraying a suspension of the considered kaolin complex into air in a reaction zone at 250°–260° C. or by spreading the considered kaolin complex in damp condition on a flat surface and placing it for 1 to 5 minutes in an oven preheated at about 250°–260° C.

In still a further embodiment of the process according to the invention the complex of kaolin with an ammonium or alkali metal salt of a carboxylic acid having more than two carbon atoms is further reacted with a quaternary ammonium salt or hydroxide of formula III, possibly in the presence of an organic solvent or diluent such as isopropanol, at a temperature between 50° and 150° C., preferably between 80° and 125° C., for at least a few minutes. According to a preferred feature of this embodiment of the invention, the symbols $R_1$, $R_2$, $R_3$ and $R_4$ in the quaternary ammonium salt or hydroxide of formula III are selected from the group comprising the alkyl radicals having from 1 to 6 carbon atoms, the phenyl-alkyl radicals in which the alkyl moyety has from 1 to 6 carbon atoms and the alkyl radicals having more than 6 carbon atoms.

Most preferably at least one of the symbol $R_1$, $R_2$, $R_3$ and $R_4$ thereby represents an alkyl radical selected from the group comprising the lauryl radical ($C_{12}$), the myristyl radical ($C_{14}$), the palmityl radical ($C_{16}$) and the stearyl radical ($C_{18}$).

According to another preferred feature of this embodiment of the invention, the process steps for preparing a kaolin complex comprising in its chemical structure a quaternary ammonium radical of formula III, are performed by using an ammonium or potassium propionate complex of kaolin as starting material.

In particular there may be used very suitably an ammonium propionate complex of kaolinite having a (001) spacing higher than 20 Å, or a potassium propionate complex of kaolinite having a (001) spacing of 16,2–16,8 Å.

According to a further preferred feature of this embodiment of the invention the ammonium or alkali metal salt complex of kaolin is dispersed in a solution of a quaternary ammonium salt of hydroxyde of formula III in an organic solvent, in an amount of about 25% by weight to about 500% by weight based on the weight of the quaternary ammonium salt or hydroxyde solution, whereby the amount of organic solvent in the solution ranges from about 20% by weight to about 200% by weight based on the weight of the quaternary ammonium salt or hydroxyde.

A most preferred organic solvent for use in the process step of this embodiment of the invention is for instance isopropanol. Preferred reaction times range from 10 to 20 minutes, preferably from 10 to 15 minutes.

The new organic complexes of kaolin materials comprising in their chemical structure quaternary ammonium radicals as obtained by the process step according to this embodiment of the invention may be used as such, in the form of the thick paste resulting from the reaction of the starting kaolin complex with a quaternary ammonium salt or hydroxide in an organic solvent, or may be washed and consequently redispersed in an excess of a further organic solvent, such as benzene or toluene.

It has however also been surprisingly found that the new organic complexes of kaolin materials comprising in their chemical structure quaternary ammonium radicals may be submitted to a treatment with aromatic hydrocarbon solvents, whereby new derivatives of the complexes are obtained which are stable in the dry form.

A further embodiment of the process according to this invention therefore comprises first reacting the complex of kaolin with amonium or alkali metal salt or a carboxylic acid having more than two carbon atoms with a quaternary ammonium salt or hydroxyde of formule III and then subjecting the obtained complex of kaolin comprising quaternary ammonium radicals in its chemical structure to a washing treatment with an aromatic hydrocarbon solvent, so as to obtain a kaolin complex derivative which is stable in the dry form.

According to a preferred feature of this embodiment of the invention the washing treatment with an aromatic hydrocarbon solvent is performed at room temperature using dry benzene, dry toluene or dry xylene.

The new products according to this invention, i.e. the new intercalation complexes of kaolin materials which comprise in their chemical structure a compound or radical selected from the ammonium salts of carboxylic acids having more than two carbon atoms, the lower alkylene glycols of formula

$$HO-CH_2-(CH_2)_n-CH_2-OH \quad II$$

in which n=0 to 4, the quaternary ammonium radicals of formula I, in which $R_1$, $R_2$, $R_3$ and $R_4$ have the meanings given hereabove, and the new type or form of the intercalation complexes of kaolin materials which comprise in their chemical structure an alkali metal salt of a carboxylic acid having more than two carbon atoms, as well as the stabilized derivatives of these complexes possess surprising and interesting properties.

Thus the kaolin-ammonium salt complexes and the kaolin-alkali metal salt complexes in accordance with the present invention, particularly the ammonium and potassium propionate complexes, are very active forms of clay which can serve as intermediates for other synthesis reactions.

The new organic complexes of kaolin material comprising in their chemical structure quaternary ammonium radicals, as well as their stabilized derivatives, on the other hand show a practically amorphous structure with respect to X-ray diffraction. They are readily dispersible in organic solvents, thereby forming stable suspensions. Further the aromatic hydrocarbon solvent treated derivatives show a good stability in the dry form.

More in general the products according to this invention appear to have interesting absorbing, dispersing, coating and lubricating properties.

They could be very useful in all those applications where a mineral loading or filler of very high specific area is required. They might for instance be used as fillers in paintings and varnishes as well as in rubbers; they could also be used as thickeners for greases, lubricants in oils, etc, as ingredients in the preparation of ointments and cosmetics, as coating materials for paper, and could find applications in drilling muds.

In these applications the kaolin complexes may be of great interest owing to the low cost of kaolin minerals and to the relative simplicity of the expansion process to obtain the same.

It has to be emphasized finally that the processes according to this invention may be carried out starting not only from well crystallized kaolins but even from poorly crystallized kaolins.

The invention will now be described more in detail in the following specific examples and the most important features of the invention will be illustrated by a number of tests and figures.

EXAMPLES AND FIGURES

EXAMPLE 1

Preparation of a kaolinite-ammonium propionate complex-small scale conditions for analytical purposes - (according to the two step embodiment of the process of the invention).

(a) First a kaolinite-hydrazine complex is prepared by reacting five grams of a soft, large crystal, paper grade Georgia kaolinite with a $d_{001}$ spacing of 7.13 Å (particle size $<2\mu$), with 50 ml of a hydrazine solution at 20°–22° C. for a few days at this temperature. The reaction mixture is stirred several times a day. Then, the reaction mixture is centrifuged and the hydrazine decanted to leave the compacted clay complex, which is used immediately.

(b) Then a kaolinite-ammonium acetate complex is prepared by treating three grams of damp kaolin-hydrazine complex (as obtained after centrifugation of the kaolin-hydrazine suspension) with an aqueous saturated solution of ammonium acetate at 20°–22° C. Each treatment consists of dispersing the kaolinite-hydrazine complex for two minutes in nine ml. of a saturated ammonium acetate solution. The suspension is then centrifuged until all the clay is compacted at the bottom of the centrifuge tube. The supernatant liquid is then decanted and replaced by a fresh solution. The treatment is repeated until 90% of the clay has been converted to the ammonium acetate complex (as controlled by X-ray diffraction) which is about five times.

(c) Three grams of the damp kaolinite-ammonium acetate complex which remains after decanting the fifth portion of ammonium acetate solution, are treated five times at 20°-22° C. with nine ml. of a saturated aqueous solution of ammonium propionate. The kaolin-ammonium acetate complex is well dispersed for two minutes in the ammonium propionate solution. The resulting suspension is centrifuged to compact the clay, after which the supernatant liquid is decanted.

By this process one obtains in very good yields a kaolinite complex of excellent purity, showing by X-ray diffraction analysis main (001) reflection peaks at 25.5 Å and 18.2 Å (see FIG. 1A). The purity of the obtained complex is illustrated by the narrowness of this reflection peaks, and by the existence of only a very week (001) reflection peak at 7.2 Å, corresponding to non-intercalated kaolinite.

Figure 2A:
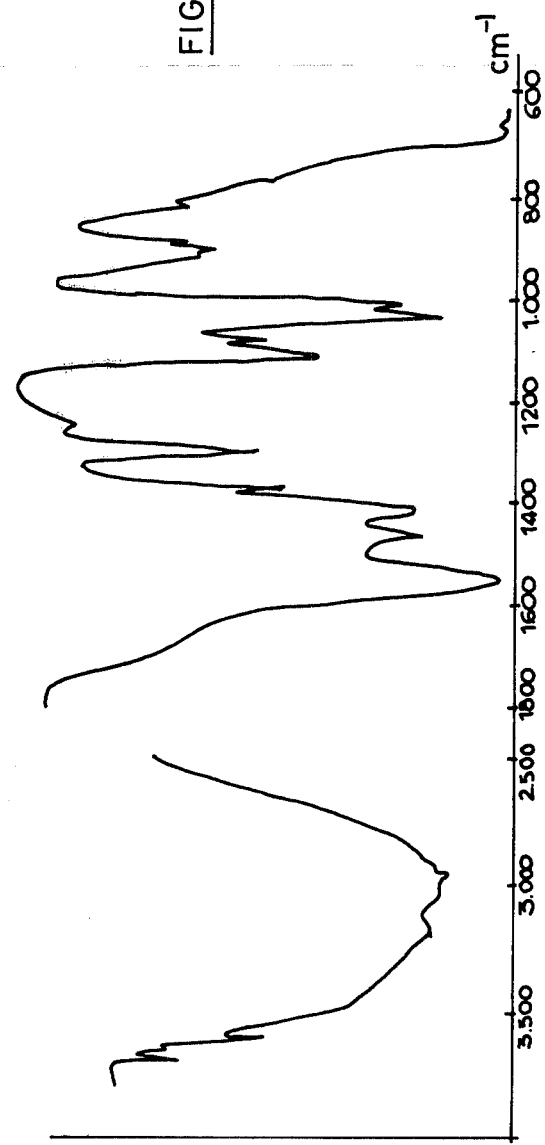
Figure 2B:
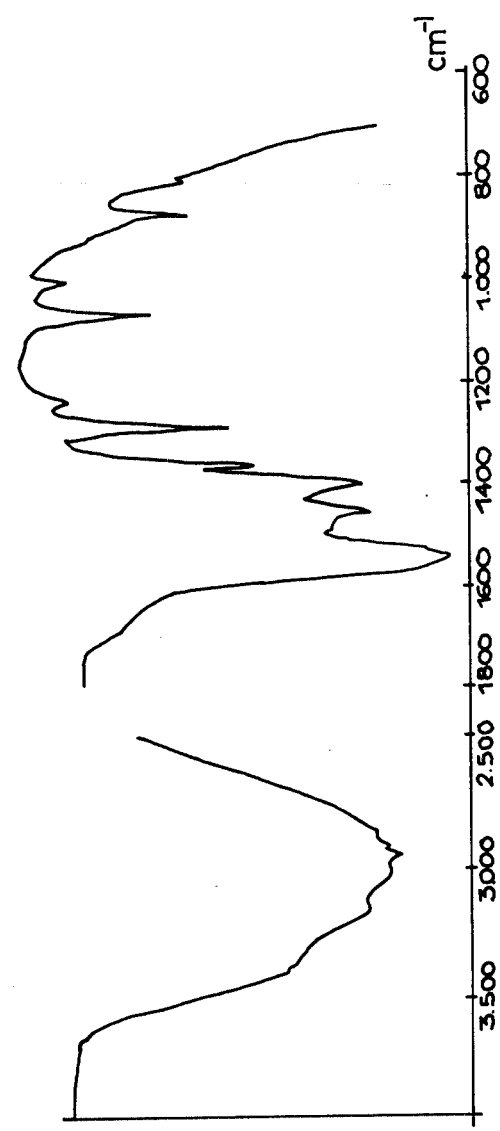
Figure 2C:
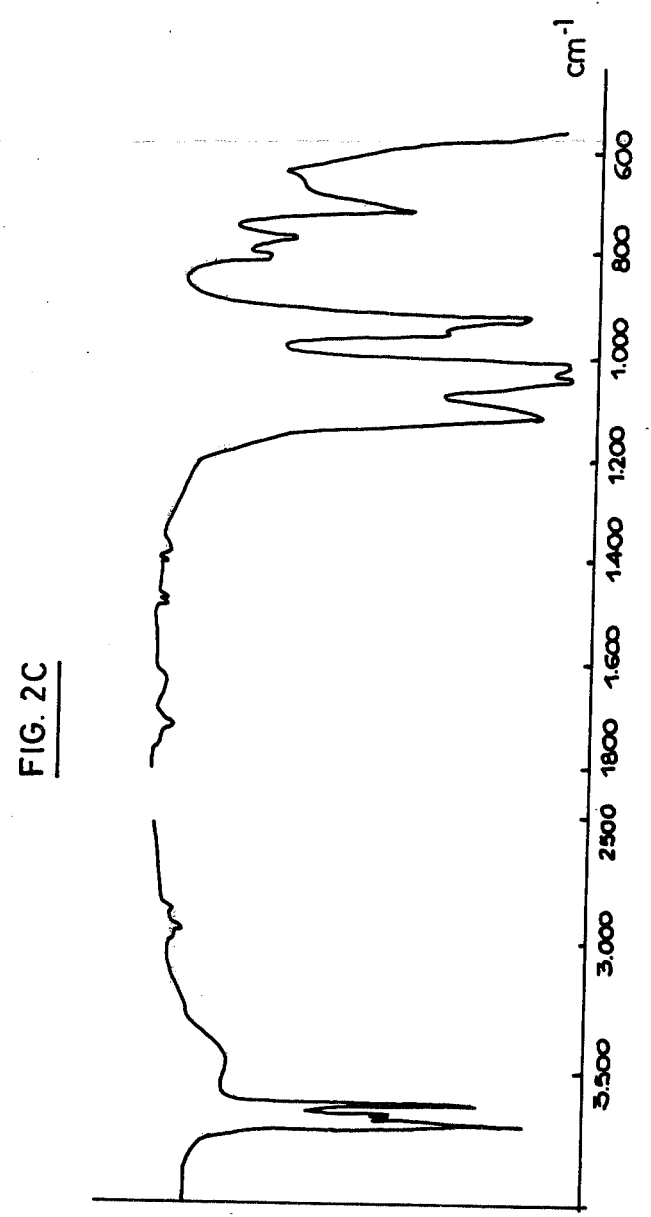

In FIG. 2 are displayed the IR spectra of pure kaolinite (2 C) of saturated aqueous ammonium propionate solution (2B) and of the complex (2A). The IR spectrum in the OH region of the complex (FIG. 2A) exhibits five v(OH) stretching bands at 3698, 3668, 3619 and 3605 $cm^{-1}$. The profile is very different from that of the starting material, which shows the first three absorption bands but in different ratios of absorbance (FIG. 2C). The fourth absorbance occurs at the slightly higher frequency of 3622 $cm^{-1}$ in pure kaolinite. The Al-OH stretching bands which appear at 938 and 913 $cm^{-1}$ in the pure clay shift to 932 and 908 $cm^{-1}$ in the complex. The remaining bands in the high and low frequency region correspond to those of pure clay or to ammonium propionate except for a shoulder at 1715 $cm^{-1}$. Water and perturbed OH bands could be hidden under the broad bands of the ammonium propionate complex.

Figure 1B:
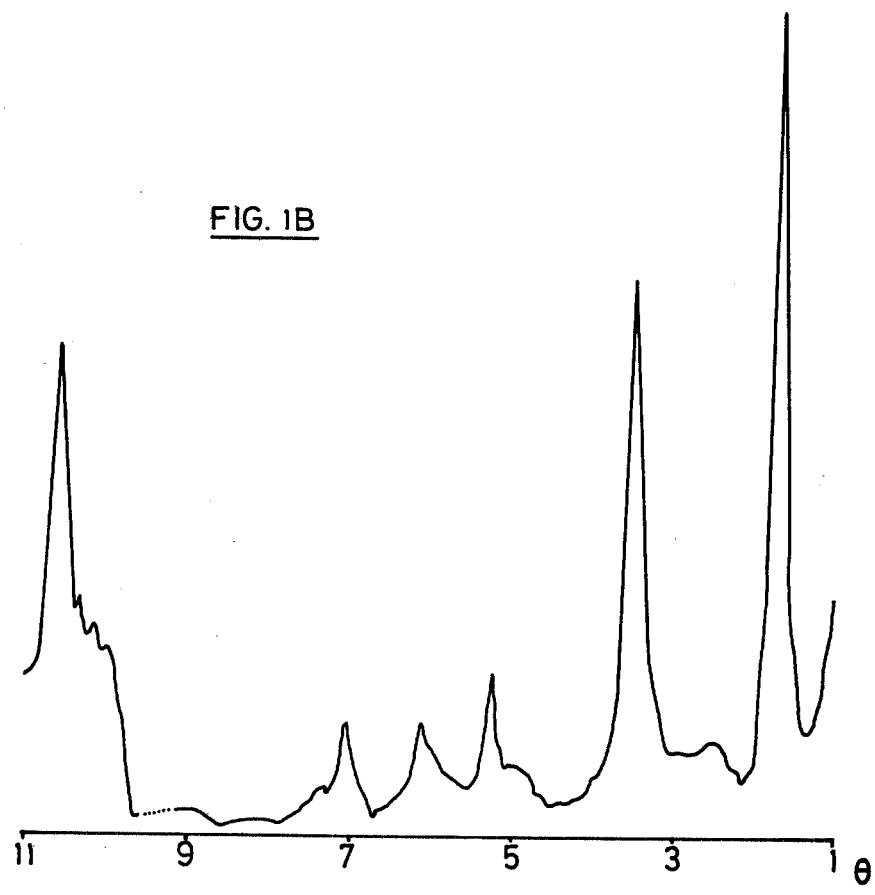

When the sample of kaolinite-ammonium propionate complex as obtained is exposed to air for about two hours, the peak due to the 25.5 Å complex increases in areas by up to 25%, while the peak due to the 18.2 Å complex becomes weaker, no orders of peaks being seen for the 18.2 Å complex (see FIG. 1B). The pure kaolinite peak remains very weak.

Figure 1C:
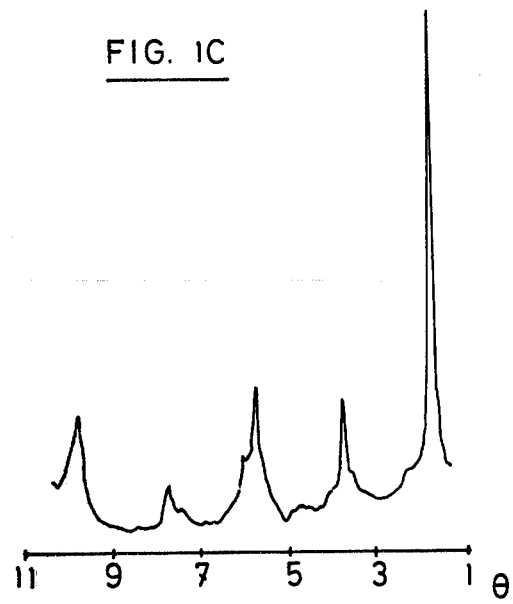

Upon treating the sample for 12 minutes with dry nitrogen, the 25.5 Å complex collapses to 23.0 Å, and at the same time a very weak peak appears at 18.4 Å (see FIG. 1C). Both complexes remain unchanged during a one hour period under nitrogen. The first and second orders of the kaolinite also remain very weak. If at this point $N_2$ is replaced by $NH_3$ gas for seven minutes, the 23.0 Å peak collapses and is replaced by a sharp, strong reflection at 22.7 Å and a very strong peak at 18.0 Å (see FIG. 1D). A small amount of kaolinite is regenerated.

Figure 1D:
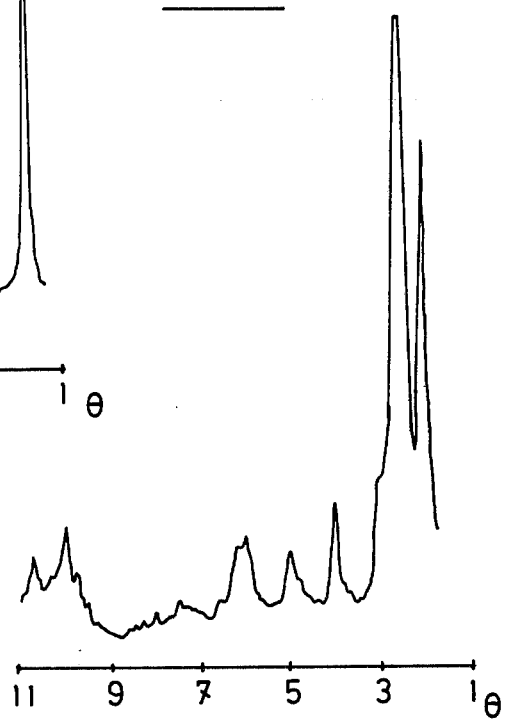
Figure 1E:
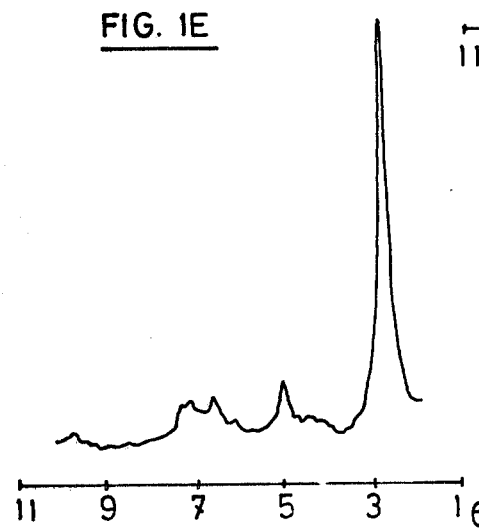

By allowing the 25.5 Å complex to remain in a desiccator over $P_2O_5$ overnight, a 19.2 Å species is produced (see FIG. 1E). After one week there is a further collapse to 17.3 Å, which after 24 hours under dry nitrogen is replaced by a peak at 14.4 Å (see FIG. 1F).

EXAMPLE 2

Preparation of a kaolinite-ammonium propionate complex-large scale conditions for semi-productive purposes—(according to the two step embodiment of the process of the invention).

1 kg of pure kaolinite is dispersed in 1800 ml of 11 M hydrazine. The obtained suspension is centrifuged during 1 hour, yielding 2 kg of kaolinite hydrazine complex and 800 ml of recovered solution.

1 kg of the obtained kaolinite-hydrazine complex is dispersed in 2000 ml of ammonium acetate solution containing 793 g of ammonium acetate per liter. The suspension is centrifuged during 1 hour, yielding 1.44 kg of kaolinite-ammonium acetate complex and 1600 ml of recovered solution.

1 kg of the obtained kaolinite-ammonium acetate complex is dispersed in 1328 ml of ammonium acetate solution containing 793 g of ammonium acetate per liter. The suspension is centrifuged during 1¼ hour, yielding 1 kg of purified kaolinite-ammonium acetate complex and 1328 ml of recovered solution. If traces of hydrazine remain in the clay these latter operations are repeated a second time.

Then 1 kg of the obtained purified kaolinite-ammonium acetate complex is dispersed in 2400 ml of ammonium propionate solution containing 835 grams of ammonium propionate per liter. The suspension is centrifuged during 1½ hour, yielding 1.138 kg of kaolinte-ammonium propionate complex and 2.265 ml of recovered solution.

1 kg of the obtained kaolinite-ammonium propionate complex is further redispersed three times in 2000 ml of ammonium propionate solution containing 835 grams of ammonium propionate per liter, centrifuging each time the obtained suspension during 1½ hour, yielding each time 1 kg of purified kaolinite-ammonium propionate complex and 2000 ml of recovered solution.

The various steps of this sequential process are reported in condensed form in table I hereinafter.

The obtained kaolinite-ammonium propionate complex shows a X-ray diffraction peak at 25.5 Å.

TABLE I.

| | | Quantities of reagents used for the preparation of the ammonium-kaolinite complex | | | | |
|---|---|---|---|---|---|---|
| Sequence | quantity of clay or complex | ml of reagent | weight of clay product | ml of solution recovered | time of centrifugation | footnote |
| 1 | 1 kg of pure kaolinite | 1800 ml 11 M hydrazine | 2 kg | 800 ml | 1 hour | a |
| 2 | 1 kg of kaolinite-hydrazine complex | 2000 ml ammonium acetate: $H_2O$: 9 mole: 1 mole | 1.44 kg | 1600 ml | 1 hour | |
| 3 | 1 kg of kaolinite-ammonium acetate complex | 1328 ml ammonium acetate: $H_2O$: 9 mole: 1 mole | 1 kg | 1328 ml | 1.25 hours | b |
| 4 | " | " | " | " | " | |
| 5 | " | 2400 ml $H_2O$: 1 mole: 1 mole | 1.138 kg | 2265 ml | 1.5 hours | d |
| 6 | 1 kg of kaolinite-ammonium propionate complex | 2000 ml ammonium propionate: $H_2O$: 1 mole: 1 mole | 1 kg | 2000 ml | 1.5 hours | |
| 7 | " | " | " | " | " | e |

TABLE I.-continued

Quantities of reagents used for the preparation of the ammonium-kaolinite complex

| Sequence | quantity of clay or complex | ml of reagent | weight of clay product | ml of solution recovered | time of centrifugation | footnote |
|---|---|---|---|---|---|---|
| 8 | " | " | " | " | " | e |

Footnotes:
a The recovered solution can be used to treat the next batch of kaolinite.
b The recovered solution can be used as the first wash solution for preparing the ammonium acetate-kaolinite complex if the volume of solution is brought up to 2000 ml by the addition of unused ammonium acetate solution. 1000 ml of ammonium acetate solution contains 793 grams of ammonium acetate.
c This step can usually be omitted. Some clays need this third washing to remove the last trace of hydrazine.
d 1000 ml of ammonium propionate solution contains 835 grams of ammonium propionate.
e The recovered solutions may be used as the first wash solution for preparing the ammonium propionate-kaolinite complex.

EXAMPLE 3

Preparation of a kaolinite-ammonium propionate complex (according to the one step embodiment of the process of the invention).

(a) First a kaolinite-hydrazine complex is prepared as described in example 1, as hereabove.

(b) Three grams of the damp kaolinite-hydrazine complex are then treated five times with an aqueous saturated solution of ammonium propionate at 20°-22° C. Each operation consists of dispersing the kaolinite-hydrazine complex for two minutes in nine ml. of ammonium propionate solution. The suspension is then centrifuged until all the clay is compacted at the bottom of the centrifuge tube. The supernatant liquid is then decanted and replaced by fresh solution. These operations are repeated five times.

By this process one obtains in reasonable yields a kaolinite complex showing by X-ray diffraction analysis a main reflection peak at 23.0 Å (see FIG. 3).

EXAMPLE 4

Preparation of a kaolinite-ammonium benzoate complex

An ammonium benzoate-kaolinite complex is prepared by treating five times at 20°-22° C. three grams of either the damp ammonium acetate-kaolin complex (as obtained according to example 1b) or the damp ammonium propionate-kaolin complex (as obtained according to example 1 or 3) with six ml. of an aqueous solution of 7 normal ammonium hydroxide saturated with ammonium benzoate. The ammonium acetate or the ammonium propionate complex is dispersed two minutes in this ammonium benzoate solution. The resulting suspension is centrifuged to compact the clay after which the supernatant liquid is decanted.

The complex, obtained in good yields and with a very good purity, shows by X-ray diffraction analysis a main reflection peak at 15.9 Å (see FIG. 4).

EXAMPLE 5

Flash treatment of kaolinite-ammonium propionate complex

Figure 6:
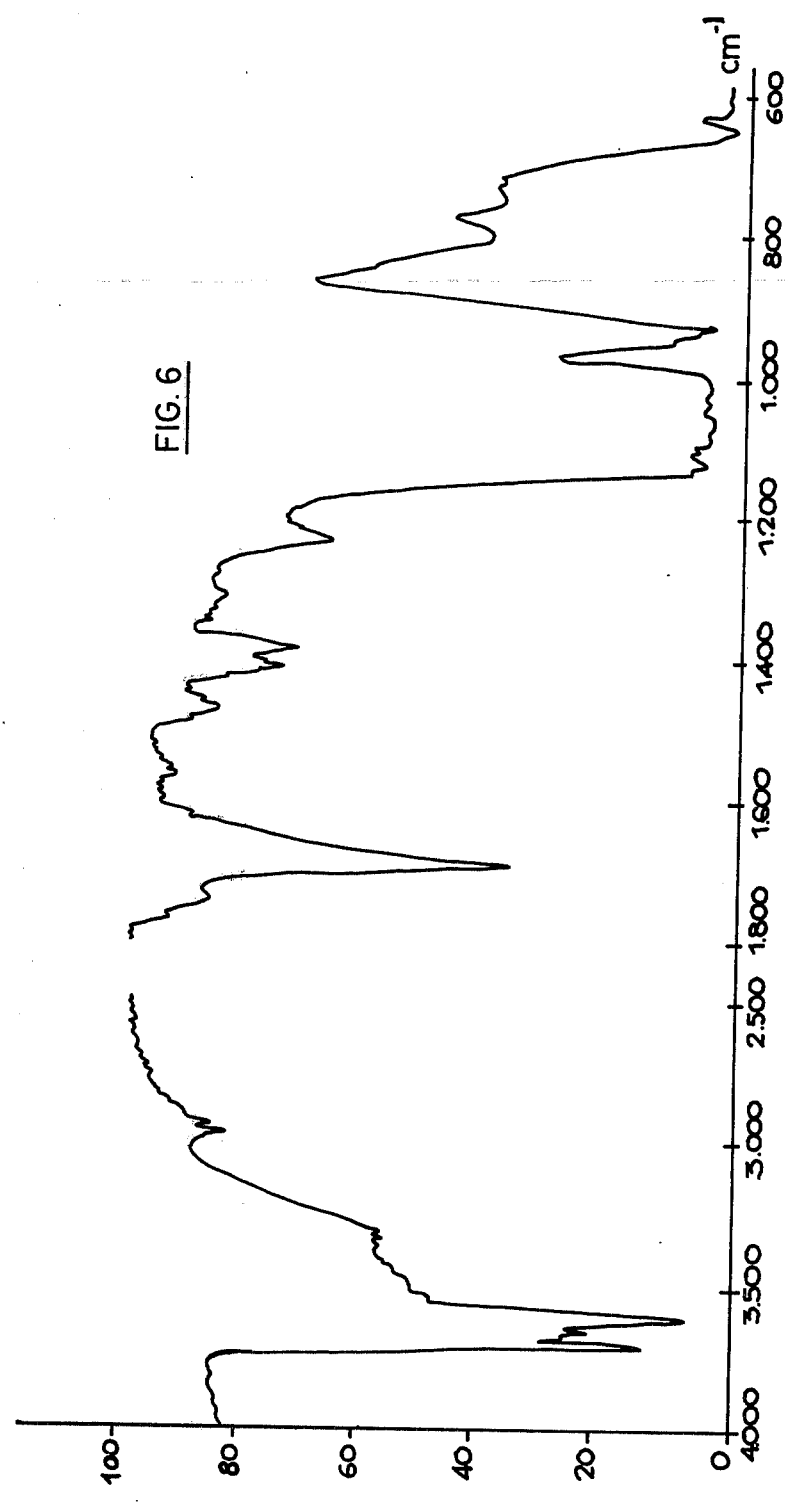

The damp kaolinite-ammonium propionate complex as obtained according to example 1 or 3 spread in a 0.4-0.5 mm. film on a glass microscope slide or a small unglazed porcelain disc. The slide or disc is placed for 2.5 minutes in an over preheated to 260° C. One obtains a stable complex showing in its X-ray diagram a main reflection peak at about 11 Å (see FIG. 5). In this stabilized complex the carboxylate (propionate) ions are bonded more directly to the AlOH sites of the clay surface than in the unstabilized kaolinite-ammonium propionate complex, as may be evidenced by the infrared spectrum of the stabilized complex (FIG. 6).

The thus obtained stabilized complexes may without any harm be kept for several weeks exposed to the ambiant air.

EXAMPLE 6

Preparation of kaolinite-potassium propionate complex (a) Starting with kaolinite-ammonium acetate complex described in example 1b, using the process described in example 1c, except that potassium propionate is used instead of ammonium propionate, one has obtained after 1.5 hours at room temperature a kaolinite-potassium propionate complex showing a main X-ray reflection at 16.2 Å.

(b) Starting with the kaolinite-hydrazine complex described in example 1a, using the process described in example 3b, except that potassium propionate is used instead of ammonium propionate, on has prepared after 1.5 hours at room temperature the same kaolinite-potassium propionate complex as in example 6a.

This potassium propionate complex, showing a main reflection at 16.2 Å may also exist in a 16.8 Å form, depending on its state of hydration. This specific type of the kaolinite-potassium propionate complex is significantly different from the type disclosed in the literature, as the latter complex shows a main reflection at 11.2 Å, and may only be obtained by reacting potassium propionate with kaolinite at 65° C. during thirty days. When the 16.2 Å potassium propionate complex is heated to 260° C. for one minute, the d-spacing falls to 12.3 Å and remains at 12.3 Å as long as the complex is maintained at 260° C. (The product has been heated for up to 30 minutes). When the previously heated product is allowed to sit in air at room temperature, the d-spacing slowly returns to 16.9 Å over a period of one day because of rehydration. The new type of potassium propionate complex is a product which is (a) easily and quickly produced; (b) stable upon storage; (c) heat resistant to 260° C. for at least 30 minutes in its 12.3 Å form.

This product may be useful for instance for the control of humidity, owing to its sufficient hydroscopicity to maintain its state of hydration.

(c) The kaolinite potassium propionate complex has also been obtained on a semi-productive scale by following the sequence of operations described in example 2, using however potassium propionate solutions instead of ammonium propionate solutions.

The obtained kaolinite-potassium complex shows an X-ray diffraction peak at 16.2-16.8 Å.

EXAMPLE 7

Reaction of kaolinite-ammonium propionate complex with ethylene glycol.

The kaolinite-ammonium complex as obtained in example 1 was washed, centrifuged and decanted five times with an excess of ethylene-glycol at room temperature. The volume of solution for each washing operation was about three times the volume of the clay complex. The reaction product was finally washed with iso-propanol to remove the excess of reagent. Care was taken in washing with iso-propanol because continued washing removes the glycol.

Figure 7A:
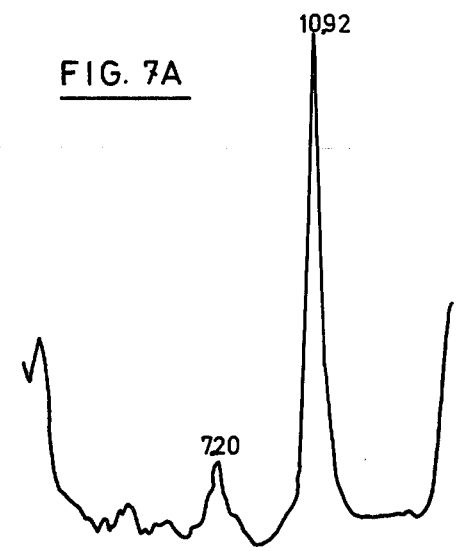

The X-ray diagram of the ethylene-glycol-treated kaolinite complex, FIG. 7A, shows a strong reflection at 10.9 Å. There is a recognizable kaolinite peak at 7.3 Å.

Figure 8A:
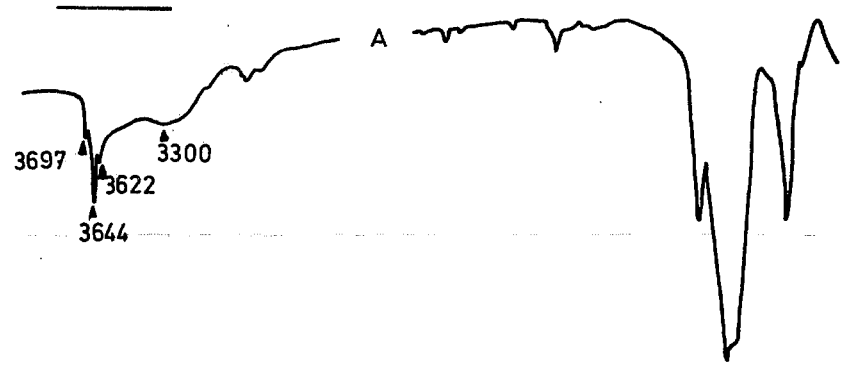

The IR spectrum of the complex, FIG. 8A, shows a highly modified OH stretching region for the kaolinite with absorptions at 3697, 3654 (very weak), 3644, and 3622 cm$^{-1}$. Table II gives the IR assignments for ethylene glycol and its intercalate.

Figure 8B:
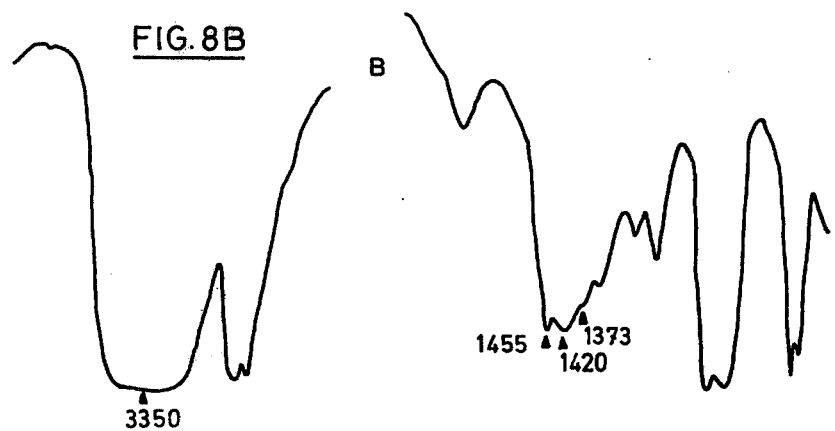

For the pure glycol, FIG. 8B, OH stretching and bending vibrations appear at 3350 and 1420 cm$^{-1}$ respectively and CH asymmetric and symmetric bending vibrations, at 1455 and 1373 cm$^{-1}$. These absorptions are rather weak for the glycol-clay complex. Significantly, no IR absorptions characteristic of ammonium propionate are observed.

On exposure of air, the complex is stable for about three hours.

TABLE II

| Infrared assignments of ethylene glycol and of its intercalates (in cm$^{-1}$). | |
|---|---|
| Frequencies | Assignment |
| 3697 | |
| 3654 | $\nu$(OH) of unperturbed |
| 3644 | kaolinite |
| 3622 | |
| 3350 | $\nu$(OH) pure glycol |
| 3300 | $\nu$(OH) of glycol hydrogen bonded to clay |
| 1455 | Asym $\delta$(CH) pure glycol |
| 1420 | $\delta$(OH) pure |
| 1373 | sym, $\delta$(CH$_2$) pure glycol |

EXAMPLE 8

Flash treatment of kaolinite-ethylene glycol complex

The kaolinite-ethylene glycol complex as obtained in example 7 was spread in damp form as a thin film on a glass plate. The glass plate was then placed for 75 seconds in an oven preheated to 260° C. After this treatment the glycol-clay complex gives and X-ray diffraction pattern containing a strong but slightly broadened peak at 9.5 Å and a weak peak of of kaolinite at 7.2 Å.

Figure 7B:
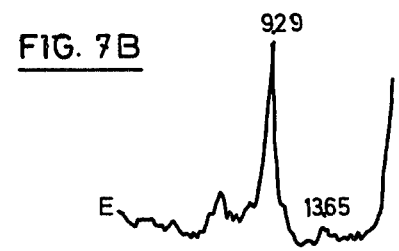

Upon heating the same sample for another 75 seconds at 260° C. the glycol-clay complex gives the X-ray diffraction pattern, represented in FIG. 7B showing reflections at 13.6 Å (broad and very weak), 9.3 Å (strong) and 7.1 Å (weak).

Figure 8C:

The Infra Red spectrum of the glycol-clay complex treated for 75 seconds at 260° C. is represented at FIG. 8C. This Infra Red spectrum shows strongly modified kaolinite OH stretching frequencies at 3697, 3660 (broad and very weak) 3622 and 3570 cm$^{-1}$. The analysis of the flash-treated kaolinite-ethylene glycol complex is in table III herebelow:

TABLE III

| Analysis of the flash-treated kaolinite-ethylene glycol complex | | |
|---|---|---|
| Chemical analysis | Moles of intercalate per gram of clay | surface area m$^2$/g |
| C : 8.21 % H : 1.65 % | 3.42 10$^{-3}$ | 876 |

EXAMPLE 9

Reaction of kaolinite-ammonium propionate complex with benzyldimethyllauryl ammonium chloride and benzyldimethylmyristyl ammonium chloride.

1.5 g of the kaolinite-ammonium propionate complex as prepared hereabove were quickly dispersed in 2.0 ml of a solution of 80 parts of a commercial undried mixture of benzyldimethyllauryl ammonium chloride and benzyldimethylmyristyl ammonium chloride, in 20 parts of isopropanol.

The dispersion of the kaolinite complex was performed under vigorous stirring in a solution at 125° C. The kaolinite complex was allowed to react for about 15 minutes.

Although in this specific example 1.5 g of kaolinite complex were dispersed in 2 ml of quaternary ammonium salt solution, it must be emphasized that up to 14 grams of complex may be added to 2 ml of solution.

The paste obtained in the present example, adding 1.5 g of kaolinite complex to 2 ml of solution, was studied as such (product A) and was washed three times with isopropanol and redispersed in an excess of dry benzene at room temperature (product B). Under these conditions rather stable suspensions are obtained.

As shown by the X-ray diffraction analysis, the reaction products A and B practically amorphous. In the X-ray spectrum there only appear very weak reflection peaks at 10 and at 3.56 Å (002-reflection of kaolinite).

Figure 9:
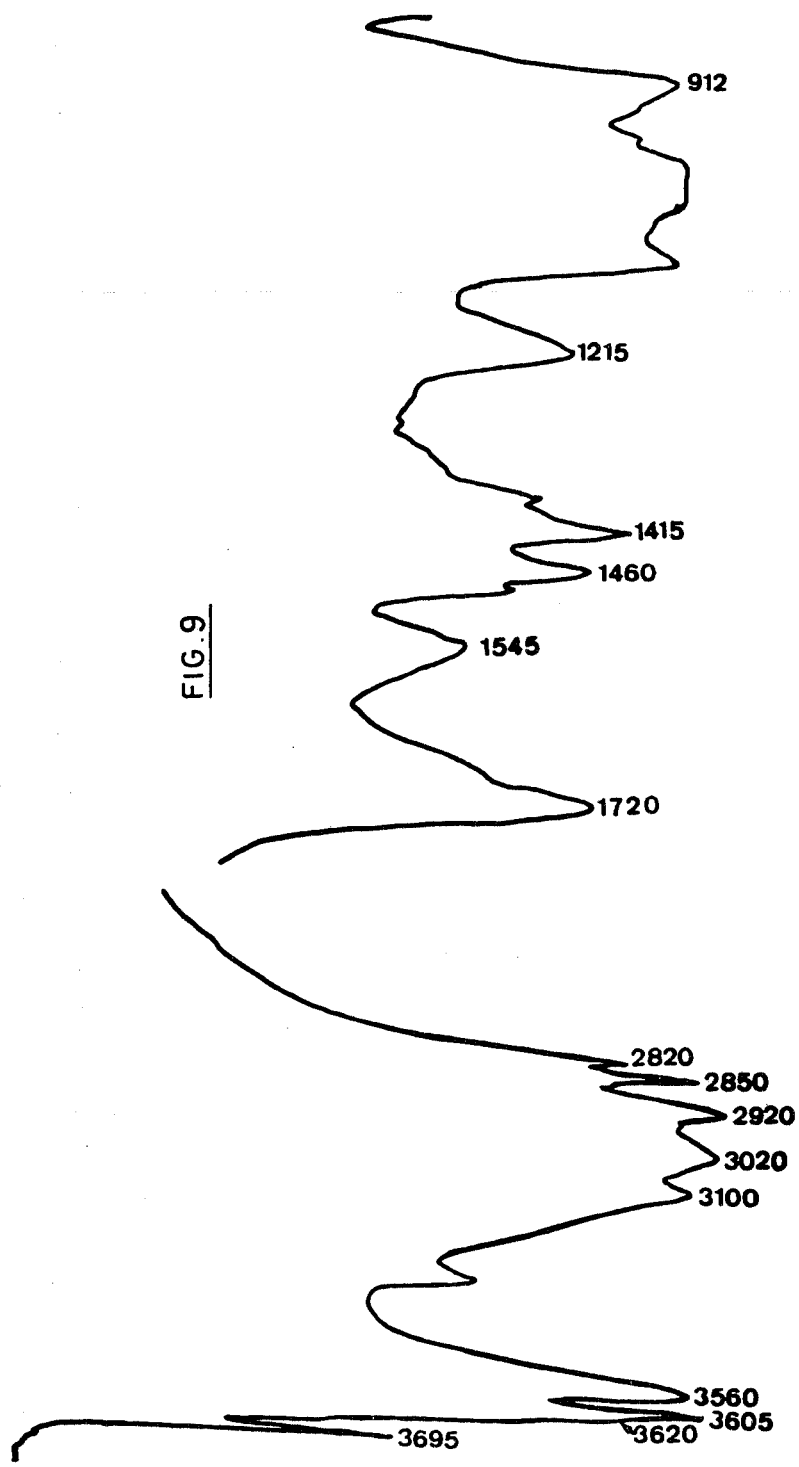
Figure 10:
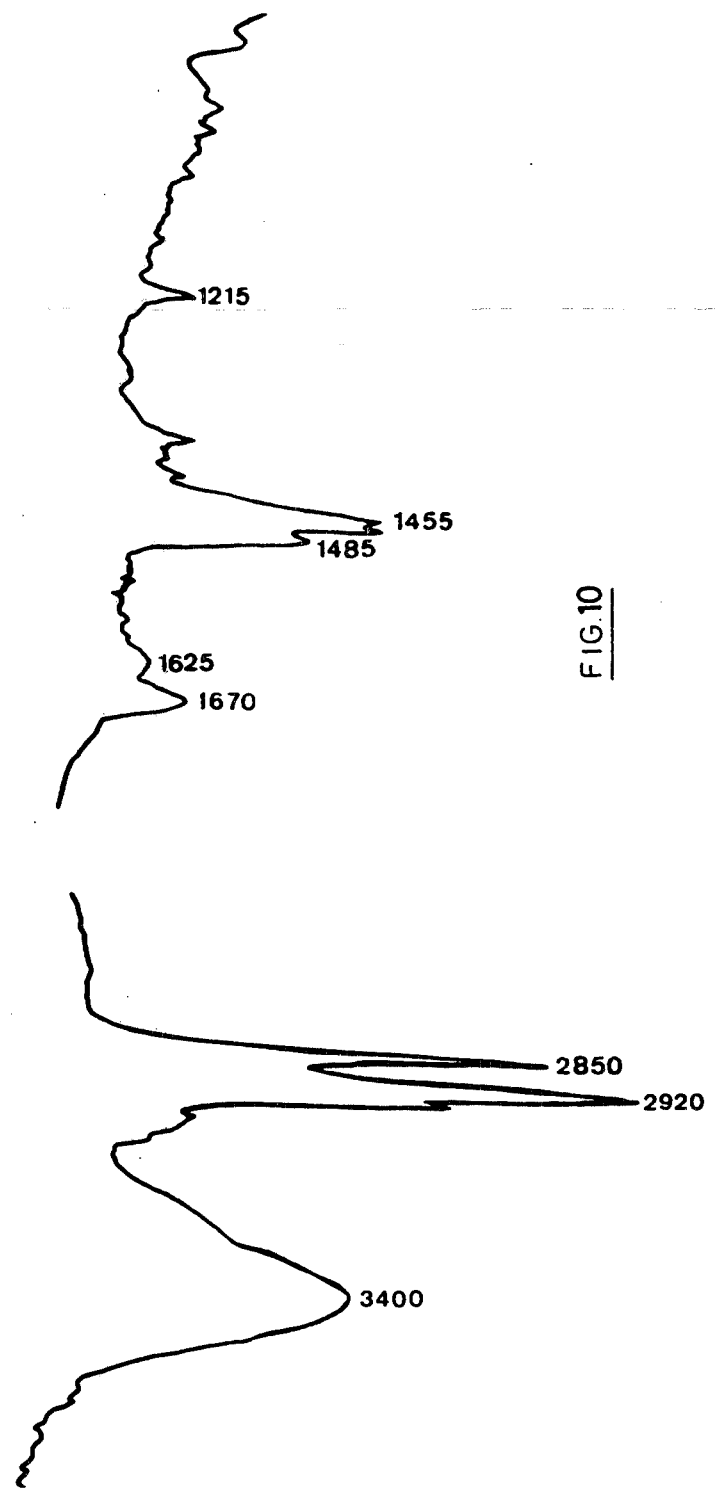

The infrared spectrum of both products A and B represented in FIG. 9, shows that the kaolinite material has been drastically modified. The infrared assignments of the observed peaks are listed in table IV hereafter. In the same table are listed the infrared assignments of the peaks observed in the infrared spectrum of the starting quaternary ammonium salt mixture (benzyldimethyllauryl ammonium chloride and benzyldimethylmyristyl ammonium chloride), which spectrum is represented in FIG. 10.

TABLE IV

| Infrared assignements of the peaks observed in the infrared spectra of: | | | |
|---|---|---|---|
| Starting mixture of quaternary ammonium salts (benzyldimethyllauryl ammonium chloride and benzyldimethylmyristyl ammonium chloride) | | Obtained organic intercalation complex of kaolinite (Products A and B) | |
| C-85 | | C-85 AP complex (120° C.) | |
| Frequencies | Assignment | Frequencies | Assignment |
| 3400 Broad | $\nu$(OH) of iso-propanol (solvent) and and H$_2$O | 3695 Sh 3650 Sh 3620 Sh 3605 S | $\nu$(OH) of clay |
| | | 3580 | $\nu$(OH) of clay perturbed |
| 3060 W 3030 W | $\nu$(CH) of benzene | 3330 | H$_2$O (?) |

TABLE IV-continued

Infrared assignements of the peaks observed in the infrared spectra of:

| Starting mixture of quaternary ammonium salts (benzyldimethyllauryl ammonium chloride and benzyldimethylmyristyl ammonium chloride) | | Obtained organic intercalation complex of kaolinite (Products A and B) | |
|---|---|---|---|
| C-85 | | C-85 AP complex (120° C.) | |
| Frequencies | Assignment | Frequencies | Assignment |
| 2950 S | | 3106 | $\nu$(OH) C$\underset{OH}{\overset{O}{\diagup}}$ |
| 2920 S | $\nu$(CH) | 3020 | $\nu$(NH) |
| 2870 Sh | aliph. | 2950 | |
| 2850 S | | 2920 | $\nu$(CH), |
| 1670 | | 2850 S | aliph. |
| 1625 | H$_2$O | 2820 S | |
| 1485 | | | |
| 1465 | asym. and sym. | 1720 | $\nu$(C=O) $\underset{OH}{\overset{O}{\diagup}}$ of C |
| 1455 | $\delta$(CH) of —CH$_3$ | 1680 Sh | |
| 1375 | and —CH$_2$— | 1545 broad | R—COO$^-$ |
| 1215 | $\nu$(C—N) | 1480 Sh | $\delta$(CH) |
| | | 1460 | |
| | | 1415 Sh | $\delta$(NH$^+_4$) |
| | | 1375 | |
| | | 1295 W Sh | |
| | | 1215 | $\nu$(C—N) |

S = sharp, I = intense, Sh = shoulder, W = weak.

The four hydroxyl stretching bands of the original kaolinite have been reduced to two bands after reaction: a very weak singlet at 3695 cm$^{-1}$, and a doublet at 3620 and 3605 cm$^{-1}$. A very strong band appears at 3550 cm$^{-1}$. The 3605 and 3550 cm$^{-1}$ bands are assigned to unperturbed and perturbed OH of the inner surface of kaolinite respectively. A singlet kaolinite OH bending band appears at 912 cm$^{-1}$. The related component at 937 cm$^{-1}$ in the original kaolinite had disappeared.

In addition, bands due to ammonium propionate and to the quaternary ammonium salts are observed.

CH stretching and deformation bands as well as the C–N band of the quaternary ammonium salts are strong. Also present are the ionized

and unionized carboxyl band. The unionized carboxyl OH stretching is at 3010 cm$^{-1}$ whereas the corresponding OH bending is at 970 cm$^{-1}$. The NH$^+_4$ deformation and stretching bands are at 1415 and 3100 cm$^{-1}$ respectively.

The observed set of interactions between the clay and the quaternary ammonium salts result therefore in the loss of stacking order about the o-axis of the clay, thus allowing the dispersibility of the obtained complexes in organic solvents.

The product B, that is the complex washed with isopropanol and redispersed in benzene forms indeed a stable suspension. On the contrary the starting kaolinite complex with ammonium propionate is not dispersible in benzene.

EXAMPLE 10

Reaction of kaolinite-potassium propionate complex with benzyldimethylpalmityl ammonium chloride and benzyldimethyl stearyl ammonium chloride.

Kaolinite-potassium propionate complex as obtained according to example 6C is reacted with a commercial, undried mixture of benzyldimethylpalmityl ammonium chloride and benzyldimethylstearyl ammonium chloride, in the same manner as described in example 9.

The products obtained according to this example have practically identical properties to those described for the products of example 9.

Thus, in particular the product obtained after washing with isopropanol and redispersion in benzene forms a stable suspension.

EXAMPLE 11

Reaction of kaolinite-potassium propionate complex with octadecyltrimethylammonium bromide.

Five grams of commercial octadecyltrimethylammonium bromide were dissolved in 10 ml of isopropanol at 80° C.

4 grams of kaolinite-potassium propionate were quickly dispersed in the hot liquid and allowed to interact for 10 minutes.

After cooling the resulting thick paste (product A) was transferred to an extraction thimble and washed for up to 5 hours with isopropanol in a soxhlet extractor. After drying overnight in air the product was dispersed in benzene (product B). Both products A and B appear as amorphous under X-ray diffraction analysis.

The infrared spectra of products A and B are very similar to that represented in FIG. 9, observed for the complexes of example 9 (aromatic quaternary ammonium salt) and show that the clay material has been drastically modified, in a similar way to that discussed in example 9 in respect to FIG. 9 and table II.

EXAMPLE 12

Reaction of kaolinite-ammonium propionate complex with octadecyltrimethyl bromide The complex of this example is obtained in the manner described in example 3 hereabove, except that one uses a kaolinite-ammonium propionate complex as starting material.

The behaviour and properties of the complex obtained starting with kaolinite-ammonium propionate complex are similar to those of the complex obtained starting with kaolinite-potassium propionate complex (example 11), except that the latter product is more resistant to washing with isopropanol.

Whereas the product resulting from the kaolinite-potassium propionate complex is well dispersed in benzene even after five hours of washing, the product resulting from the kaolinite-ammonium propionate complex is but poorly dispersed in benzene after 3 hours of washing.

EXAMPLE 13

Preparation of stabilized derivatives of the complexes as obtained according to examples 9 and 10

The products as obtained according to examples 9 and 10 hereabove were each washed with xylene at 140° C. The obtained products were dried and showed a remarkable stability in the dry form, even when exposed for over three days to atmospheric mosture.

Figure 11:
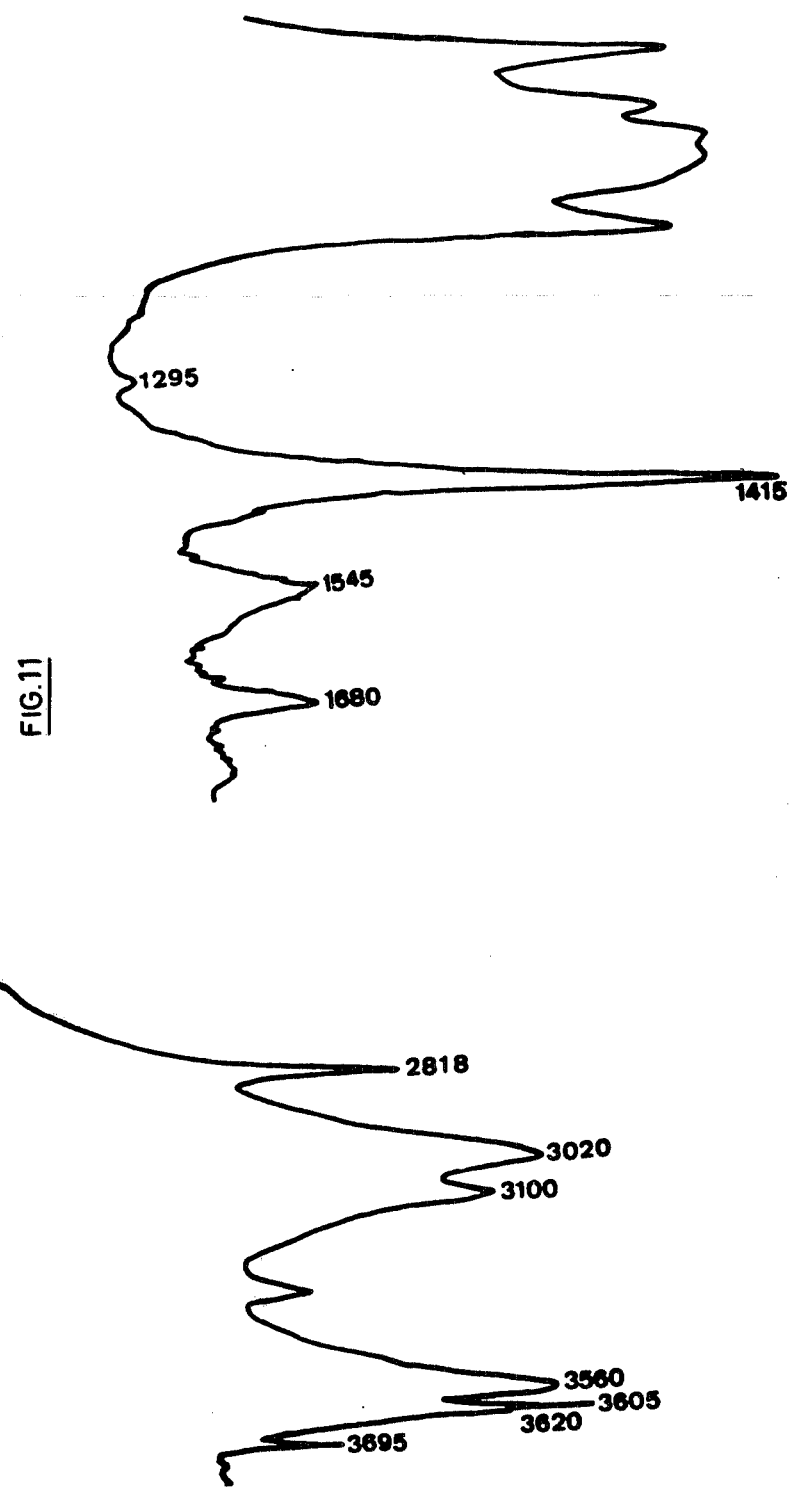

In this dry state, redispersion of the products in benzene is readily obtained. The products are however not stable in water. Each of the products obtained according to this example, by washing the products of examples 9 and 10 with xylene (or in the same manner with benzene or toluene) show practically the same infrared spectra (FIG. 11).

The infrared assignments of the observed peaks are listed in table V hereafter.

TABLE V

Infrared assignements of the peaks observed in the infrared spectrum of the complexes of examples 9 and 10, after washing 140° C. with xylene.

| Frequencies (cm$^{-1}$) | | Assignment |
|---|---|---|
| 3695 | | |
| 3650 | W Sh | |
| | | $\nu$ (OH) of clay |
| 3620 | S Sh | |
| 3605 | I | |
| 3560 | | perturbed |
| | | $\nu$ (OH) of clay |
| 3330 | | H$_2$O (?) |
| 3100 | | |
| | | $\nu$(OH) in C$\underset{OH}{\overset{O}{\diagup\!\!\!\diagdown}}$ |
| 3020 | | $\nu$(NH) |
| 2818 | S | $\nu$(CH) aliph. (?) |
| 1680 | | $\nu$ (C=O) |
| 1545 | broad | R—COO$^-$ |
| 1415 | S | (NH$^+_4$) |
| 1295 | W | $\nu$(C—N) |

S = sharp, I = intense, Sh = shoulder, W = weak.

When comparing the data of table V to the data of table IV, one readily observes that upon washing the complexes according to examples 9 and 10, the quaternary ammonium is almost completely displaced, but the other spectroscopic features remain.

The unionized carboxyl shows up as a doublet at 1720 and 1680 cm$^{-1}$ in the unwashed samples and as a single band at 1680 cm$^{-1}$ in the samples washed with xylene (or benzene or toluene).

Thus, there is also for these stabilized derivatives obtained by washing the quaternary ammonium-kaolinite complexes according to the invention with xylene (or toluene or benzene) observed a loss of stacking order about the c-axis of the clay.

This phenomenom is further accompagnied by a curling of the layer packets of the kaolin material (as shown by high resolution micrographs of kaolinite complex crystals) which seems further to improve the dispersibility of the complexes in organic solvents.

It may be further stated that treating the stabilized derivatives according to this example with water restores the X-ray diffraction pattern and the IR-spectrum of a disordered kaolinite.

In connection with the above examples 1 to 6 it must be emphasized that the invention is not limited in these embodiments to treating the kaolins and kaolin complexes with aqueous solutions, the choice of the solvents used being only directed by imperatives of solubility. In particular one may also use in these embodiments solutions of the ammonium or alkaline metal salts in alcohols, for example isopropanol.

Moreover, to clearly put in evidence the novelty of the present invention with respect to the known art, one may point out the following chracteristics of the compounds according to the invention as compared to those of the known compounds in the same field of technology.

The kaolinite-ammonium acetate complex is a known complex, obtained by reacting kaolinite with a saturated solution of ammonium acetate. This kaolinite-ammonium acetate complex shows a main reflection at about 14 Å. The new kaoline-ammonium carboxylate complexes however have larger characteristic equidistances between the silicate layers. The ammonium propionate complex for example shows a main reflection at about 25.5 Å. Therefore, as the equidistance of the silicate layers is larger in the new complexes, the cohesion between successive layers is much lower in said new complexes.

Accordingly, they show a greater reactivity and versability than the known ammonium acetate complexes.

Further, the crystallographic definition of the new complexes is much better than that of the known complexes.

Finally, an important difference between the known complex and the new complexes of kaolin materials with ammonium salts of dicarboxylic acids lies in the fact that, upon flash decomposition, the known complex (ammonium acetate complex) does not yield a stable product, whereas the ammonium carboxylate complexes according to the invention yield stable species.

Flash decomposition of ammonium acetate-kaolinite complex yields a product having a 11.7 Å spacing, which product is highly labile and regenerates after two days the initial kaolinite. In this respect it may be recalled that the ammonium propionate flash product is stable for many days at room temperature.

In the attached drawings, the FIGS. 1 to 6 represent X-ray and I.R. spectra as stated hereafter:

FIG. 1A: X-ray spectrum of 25.5 Å/18.2 Å ammonium propionate complex

FIG. 1B: X-ray spectrum of pure 25.5 Å ammonium propionate complex

FIG. 1C: X-ray spectrum of 23.0 Å ammonium propionate complex

FIG. 1D: X-ray spectrum of the 18.0 Å ammonium propionate complex

FIG. 1E: X-ray spectrum of the 19.2 Å ammonium propionate complex

Figure 1F:
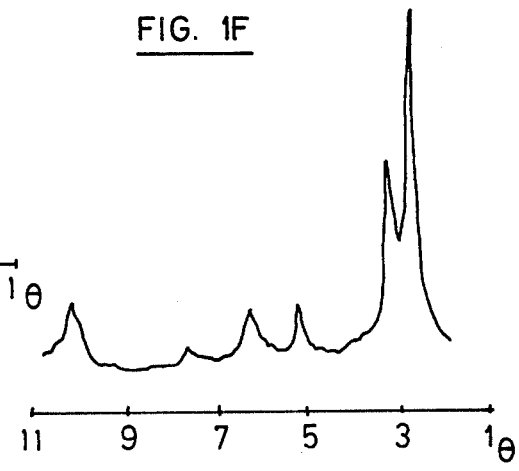

FIG. 1F: X-ray spectrum of the 14.4 Å ammonium propionate complex

FIG. 2A: IR spectrum of 25.5 Å ammonium propionate complex

FIG. 2B: IR spectrum of ammonium propionate solution

FIG. 2C: IR spectrum of pure kaolinite

FIG. 3: X-ray spectrum of 23.0 Å ammonium propionate complex prepared directly from kaolin-hydrazine complex FIG. 4: X-ray spectrum of ammonium benzoate complex FIG. 5: X-ray spectrum of flash heated ammonium propionate complex FIG. 6: IR spectrum of flash heated ammonium propionate complex FIG. 7A: X-ray spectrum of ethylene glycol complex FIG. 7B: X-ray spectrum of flash heated ethylene glycol complex FIG. 8A: IR spectrum of ethylene glycol complex FIG. 8B: IR spectrum of pure ethylene glycol complex FIG. 8C: IR spectrum of flash heated ethylene glycol complex FIG. 9: IR spectrum of quaternary ammonium complex FIG. 10: IR spectrum of starting quaternary ammonium salt FIG. 11: IR spectrum of stabilized derivative of quaternary ammonium complex.

What is claimed is:

1. Process for preparing new intercalation complexes of kaolin materials having organic compounds or radicals in their chemical structure, said compounds or radicals being selected from the ammonium salts of carboxylic acids having more than two carbon atoms, the alkali metal salts of carboxylic acids having more than two carbon atoms, said process comprising (1) reacting a member selected from the group consisting of a kaolin-hydrazine complex and a kaolin-ammonium acetate complex with a solution of an ammonium or alkali metal salt of a carboxylic acid having more than two carbon atoms.

2. Process according to claim 1, in which the kaolin-hydrazine complex is reacted with a saturated aqueous solution of an ammonium or alkali metal salt of a carboxylic acid having more than two carbon atoms.

3. Process according to claim 2 in which the kaolin-hydrazine complex is washed with one or more fractions of saturated aqueous solution of an ammonium or alkali metal salt of a carboxylic acid having more than two carbon atoms, and thereafter thoroughly draining the obtained product after each operation.

4. Process according to claim 1 in which the kaolin-hydrazine complex is first reacted with a saturated aqueous solution of ammonium acetate, whereafter the obtained kaolin-ammonium acetate is reacted with a saturated solution of an ammonium or alkali metal salt of a carboxylic acid having more than two carbon atoms.

5. Process according to claim 4 in which the kaolin-hydrazine complex is first washed with two or more fractions of a saturated aqueous solution of ammonium acetate, the obtained product being thoroughly drained after each washing operation, whereafter, the obtained kaolin-ammonium acetate complex is washed with two or more fractions of a saturated aqueous solution of an ammonium or alkali metal salt of a carboxylic acid having more than two carbon atoms, the obtained product being thoroughly drained after each washing operation.

6. Process according to claim 1, in which the obtained intercalation complex of kaolin is further subjected to a flash-heat treatment at a temperature of about 100°-300° C. so as to obtain a stabilized intercalation complex of kaolin and an ammonium salt of a carboxylic acid having more than two carbon atoms.

7. Process according to claim 1 in which the complex of kaolin with an ammonium or alkali metal salt of a carboxylic acid having more than two carbon atoms is further reacted with an excess of a lower alkylene glycol of the formula II, for at least a few minutes

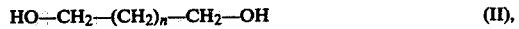

HO—CH$_2$—(CH$_2$)$_n$—CH$_2$—OH  (II), in which n=0 to 4, so as to obtain a complex of kaolin having a lower alkylene glycol of formula II in its chemical structure.

8. Process according to claim 7 in which the reaction with the lower alkylene glycol is performed at room temperature.

9. Process according to claim 7 in which the lower alkylene glycol is ethylene glycol.

10. Process according to claim 7 in which the complex of kaolin is with ammonium or potassium propionate, and such is further reacted with the lower alkylene glycol of formula II.

11. Process according to claim 7 in which the complex of kaolin is further reacted with the lower alkylene glycol of formula II, whereafter the obtained intercalation complex of kaolin is subjected to a flash heat treatment at a temperature of about 100°-300° C. so as to obtain a stabilized intercalation complex of kaolin and the lower alkylene glycol.

12. Process according to claim 1, in which the obtained complex of kaolin with an ammonium or alkali metal salt of a carboxylic acid having more than two carbon atoms is further reacted with a quaternary ammonium salt or hydroxide of formula III at a temperature between 50° and 150° C. for at least a few minutes

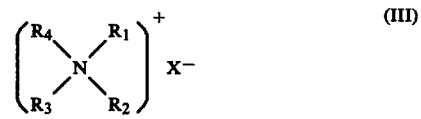

in which R$_1$, R$_2$, R$_3$ and R$_4$ each represent a group selected from aliphatic and aromatic hydrocarbon radicals and in which X represents the anion of a mineral acid or a hydroxyl radical, so as to obtain a complex of kaolin containing in its chemical structure quaternary ammonium radicals of formula

in which R$_1$, R$_2$, R$_3$ and R$_4$ have the meanings given above.

13. Process according to claim 12 in which in the quaternary ammonium salt of hydroxide of formula III in which R$_1$, R$_2$, R$_3$ and R$_4$ are selected from the group consisting of alkyl radicals having from 1 to 6 carbon atoms, phenylalkyl radicals in which the alkyl moiety has from 1 to 6 carbon atoms and alkyl radicals having more than 6 carbon atoms.

14. Process according to claim 12, in which in the quaternary ammonium salt or hydroxide of formula III at least one of the groups R$_1$, R$_2$, R$_3$ and R$_4$ represents an alkyl radical selected from the group consisting of a lauryl radical, a myristyl radical, a palmityl radical and a stearyl radical.

15. Process according to claim 12, in which the complex of kaolin is with ammonium or potassium propionate.

16. Process according to claim 12, in which the ammonium or alkali metal salt complex of kaolin is dispersed in the solution of a quaternary ammonium salt or hydroxide of formula III in an organic solvent, in an amount of about 25% by weight to about 500% by weight based on the weight of the quaternary ammonium salt or hydroxide solution, whereby the amount of organic solvent in the solution ranges from about 20% by weight to about 200% by weight based on the weight of the quaternary ammonium salt or hydroxide.

17. Process according to claim 12, in which the complex of kaolin with an ammonium or alkali metal salt of a carboxylic acid having more than two carbon atoms is first reacted with the quaternary ammonium salt or hydroxide of formula III, whereafter the obtained complex of kaolin containing quaternary ammonium radicals in its chemical structure is subjected to a washing with an aromatic hydrocarbon solvent, so as to obtain a kaolin complex derivative which is stable in the dry form.

18. Process according to claim 17, in which the washing solvent is selected from the group consisting of dry benzene, dry toluene and dry xylene.

19. Intercalation complexes of kaolin materials with ammonium salts of carboxylic acids having more than two carbon atoms.

20. Kaolin-ammonium propionate complex.

21. Kaolin-ammonium benzoate complex.

22. Kaolinite potassium propionate complex showing in its X-ray diagram a main reflection at about 16.2 Å–16.8 Å.

23. Intercalation complexes of kaolin materials with lower alkylene glycols of formula

$HOCH_2-(CH_2)_n-CH_2OH$      (II), in which n=0 to 4.

24. Kaolin-ethylene glycol complex.

25. Intercalation complexes of kaolin materials comprising in their chemical structure quaternary ammonium radicals of the formula

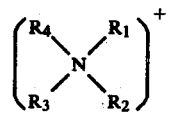

in which $R_1$, $R_2$, $R_3$ and $R_4$ each represent a group selected from the aliphatic and aromatic hydrocarbon radicals.

26. Intercalation complexes according to claim 19, in which $R_1$, $R_2$, $R_3$ and $R_4$ are selected from the group consisting of alkyl radicals having from 1 to 6 carbon atoms, phenylalkyl radicals in which the alkyl moiety has from 1 to 6 carbon atoms and alkyl radicals having more than 6 carbon atoms.

27. Intercalation complexes according to claim 19, in which at least one of the groups $R_1$, $R_2$, $R_3$ and $R_4$ represents an alkyl radical selected from the group consisting of a lauryl radical a myristyl radical a palmityl radical and a stearyl radical.

28. Stabilized derivative of kaoliniteammonium propionate complex showing in its X-ray diagram a main reflection peak at about 11 Å.

29. Stabilized derivative of kaolinite-ethylene glycol complex showing in its X-ray diagram a main reflection peak at about 9.5 Å.

30. The process of claim 12, wherein said further reaction with a quaternary ammonium salt or hydroxide of formula III is in the presence of a member selected from the group consisting of an organic solvent and diluent.

31. The process of claim 30, wherein said member is isopropanol.